United States Patent [19]

Datema et al.

[11] Patent Number: 5,215,971

[45] Date of Patent: Jun. 1, 1993

[54] ANTIVIRAL PHARMACEUTICAL COMPOSITION COMPRISING 5-SUBSTITUTED PYRIMIDINE NUCLEOSIDES

[75] Inventors: Roelf Datema, Cheshire, Conn.; Kristina B. Gotthammar, Saltsjo-Boo; Karl N. G. Johansson, Enhörna, both of Sweden; Zsuzsanna M. I. Kovacs, Pietra Ligure, Italy; Björn G. Lindborg, Älvsjö, Sweden; Goran B. Stening, Södertälje, Sweden; Bo F. Öberg, Uppsala, Sweden

[73] Assignee: Medivir AB, Stockholm, Sweden

[21] Appl. No.: 726,738

[22] Filed: Jul. 2, 1991

Related U.S. Application Data

[63] Continuation of Ser. No. 559,999, Jul. 31, 1990, abandoned, which is a continuation of Ser. No. 309,049, Feb. 8, 1989, abandoned, which is a continuation-in-part of Ser. No. 131,022, Dec. 10, 1987, abandoned.

[30] Foreign Application Priority Data

Dec. 19, 1986 [SE] Sweden .................. 8605503

[51] Int. Cl.$^5$ .................. A61K 31/70; C07H 17/00
[52] U.S. Cl. .................. 514/49; 536/28.54; 514/894
[58] Field of Search .................. 536/23; 514/49, 58, 514/894

[56] References Cited

U.S. PATENT DOCUMENTS

| 3,328,388 | 6/1967 | Shen et al. | 536/23 |
| 3,642,771 | 2/1972 | Gauri | 536/23 |
| 4,247,544 | 1/1981 | Bergstrom et al. | 514/50 |
| 4,267,171 | 5/1981 | Bergstrom et al. | 536/23 |
| 4,344,937 | 8/1982 | Machida | 514/50 |
| 4,386,076 | 5/1983 | Machida et al. | 536/23 |

FOREIGN PATENT DOCUMENTS

| 208550 | 1/1987 | European Pat. Off. |
| 1620185 | 2/1970 | Fed. Rep. of Germany |
| 2915254 | 11/1979 | Fed. Rep. of Germany |
| 3036131 | 4/1981 | Fed. Rep. of Germany |
| 3045375A1 | 7/1982 | Fed. Rep. of Germany |
| 8400759 | 3/1984 | PCT Int'l Appl. |
| 2060604 | 5/1981 | United Kingdom |
| 1601020 | 10/1981 | United Kingdom |

OTHER PUBLICATIONS

Chang Chu et al, J. Med. Chem. 32: 612-617 1989.

(List continued on next page.)

Primary Examiner—John W. Rollins
Attorney, Agent, or Firm—Birch, Stewart, Kolasch & Birch

[57] ABSTRACT

Use of a compound of the formula

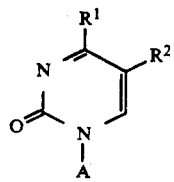

wherein
A is β-2'-deoxy-D-ribofuranosyl or β-D-arabinofuranosyl;
$R^1$ is hydroxy or amino;
$R^2$ is cycloalkyl or alkyl-substituted cycloalkyl containing 1-5 carbon atoms; saturated or unsaturated, straight or branched alkyl containing 1-5 carbon atoms which may be unsubstituted or substituted with halogen, hydroxy, mercapto, trifluoroalkyl or difluoroalkyl containing 1-3 carbon atoms, phenoxy or alkoxy containing 1-3 carbon atoms; phenyl or phenylalkyl containing 1-3 carbon atoms in the alkyl part, or a physiologically acceptable salt thereof, for manufacture of a medicament for therapeutic or prophylactic control or treatment of retrovirus, especially HIV, or hepatitis B virus infections in animal and man and to a method of such treatment.

15 Claims, No Drawings

OTHER PUBLICATIONS

De Clercg, Methods and Findings in Experimental and Clinical Pharmacology, vol. 2, No. 5 (1980).
Widell et al, Antiviral Res., 6(2), 103-12 (1986).
De Clercq, Mol. Pharmcol., 19(1), 122-9 (1981).
Robin, C & EN, Jan. 27, 1986.
Ruth et al. "C-5 Substituted Pyrimidine Nucleosides. 1. Synthesis of C-5 Allyl, Propzl, and Propenyl Uracil and Cystosine Nucleosides via Organopalladium Intermediates" J. Org. Chem., vol. 43, No. 14 (1978).
Balzarini et al. "5-Substituted 2'-Deoxyuridines: Correlation Between Inhibition of Tumor Cell Growth and Inhibition of Thymidine Kinase and Thymidylate Synthetase", Biological pharmacology, vol. 31, No. 22: 3673-3682 (1982).
De Clercq et al., "Nucleoside Analogs with Selective Antiviral Activity", J. Carbohydrates Nucleosides-Nucheotides, vol. 5, No. 3: 187-224 (1978).
Tao et al., J. Medical Virology, "Inhibition of Human Hepatitus B Virus DNA Polymerase and Duck Hepatitus B Virus Polymerase by Triphosphatis of Triphosphates of Thymidine Analogs and Pharmacokinatic Properties of the Corresponding Nucleosides".
Nordenfelt et al., J. Medical Virology, 22: 231-36 (1987).
Vrang et al., Antimicrobial Agents and Chemotherapy, p. 867-872 (May 1986) vol. 29, No. 5.
Oberg, "Antiviral Therapy", IV International Conference on AIDS, Stockholm 1988, AIDS Research in Press.
I. Basnak et al.: Coll. Czech. Chem. Commun. 51(8) 1986, pp. 1764-1771.
A. Holy et al.: Nucleic Acids Research Symp. Ser. No. 18, 1987, pp. 69-73.
E. DeClerq et al.: J. Med. Chem. 26(5), 1983, pp. 661-666.

ANTIVIRAL PHARMACEUTICAL COMPOSITION COMPRISING 5-SUBSTITUTED PYRIMIDINE NUCLEOSIDES

This application is a continuation of application Ser. No. 07/559,999 filed on Jul. 31, 1990, which is a continuation of application Ser. No. 07/309,049 filed on Feb. 8, 1989, which is a continuation-in-part of application Ser. No. 07/131,022 filed on Dec. 10, 1987, the entire contents of which are incorporated herein by reference, and all now abandoned.

FIELD OF THE INVENTION

The present invention relates to the use of chemical compounds and physiologically acceptable salts thereof for the therapeutic and prophylactic control and treatment of the Acquired Immuno Deficiency Syndrome (AIDS), hepatitis B virus infections and retrovirus infections and method for such control and treatment in animal and man.

BACKGROUND OF THE INVENTION

In the late seventies a new disease was reported, which subsequently was referred to as Acquired Immuno Deficiency Syndrome (AIDS). It is now generally accepted that a retrovirus referred to as Human T-cell Lymphotropic Virus (HTLV-III) or Lymphadenopathy Associated Virus (LAV) plays an essential role in the etiology of AIDS. This virus will herebelow be denoted by the new name HIV (Human Immunodeficiency Virus).

The full-blown AIDS is characterized by a profound immunodeficiency due to low numbers of a subset of lymphocyte-T-helper cells, which are one target for HIV infection. The profound immunodeficiency in the full-blown AIDS patients makes these patients highly susceptible to a variety of opportunistic infections of bacterial, fungal, protozoal or viral etiology. The etiological agents among viral opportunistic infections are often found in the herpes virus group, i.e., Herpes simplex virus (HSV), Varicella Zoster virus (VZV), Epstein-Barr virus (EBV) and, especially, cytomegalovirus (CMV). Other retroviruses affecting humans are HTLV-I and II and examples of retroviruses affecting animals are feline leukemia virus and equine infections anaemia virus.

Hepatitis B virus infections cause severe disease such as acute hepatitis, chronic hepatitis, fulminant hepatitis in a considerable number of persons. It is estimated that there are 200 million patients with chronic hepatitis B infection in the world. A considerable number of the chronic cases progress to liver cirrhosis and liver tumours. In some cases the hepatitis infections also take a rapid and severe course as in fulminant B hepatitis with about 90% mortality. At present there is no known effective treatment against hepatitis B infections.

PRIOR ART

Several nucleosides of the formula I below are known compounds. Some of the compounds are described for instance in J. Med. Chem. 26(9),1252-7, J. Org. Chem. 43(14), 2870-6, DD 114949, U.S. Pat. No. 4247544 and GB 1601020.

DISCLOSURE OF THE INVENTION

It has been found according to the present invention that the compounds of the formula

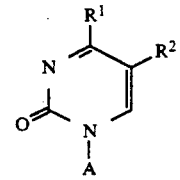

wherein

A is β-2'-deoxy-D-ribofuranosyl or β-D-arabinofuranosyl;

$R^1$ is hydroxy or amino;

$R^2$ is cycloalkyl or alkyl-substituted cycloalkyl containing 1-5 carbon atoms; saturated or unsaturated, straight or branched alkyl containing 1-5 carbon atoms which may be unsubstituted or substituted with halogen, hydroxy, mercapto, trifluoroalkyl or difluoroalkyl containing 1-3 carbon atoms, phenoxy or alkoxy containing 1-3 carbon atoms; phenyl or phenylalkyl containing 1-3 carbon atoms in the alkyl part, or a physiologically acceptable salt thereof, present a new possibility to block the multiplication of retrovirus and hepatitis B virus, respectively, by use a nucleoside analogue of said formula. Accordingly, the nucleoside analogues of said formula and physiologically acceptable salts thereof have unobvious and beneficial properties as prophylactic and/or therapeutic agents in the control or treatment of retrovirus and hepatitis B virus infections, respectively. Said nucleosides are especially interesting as agents capable of inhibiting the activity of the HIV in man.

All retroviruses, including HIV, require an enzyme called reverse transcriptase in their natural cycle of replication.

Hepatitis B virus (HBV) is a DNA virus with a unique circular double-stranded DNA genome which is partly single-stranded. It contains a specific DNA polymerase required for viral replication. This DNA polymerase also acts as a reverse transcriptase during the replication of HBV DNA via an RNA intermediate.

The compounds of the invention can be transformed by cells or enzymes to triphosphates which inhibit the activity of reverse transcriptase of retrovirus and the activity of DNA polymerase of hepatitis B virus.

Individual compounds within the formula I may be novel.

The known compounds as well as the novel compounds of formula I are prepared in known manner as is described in the literature.

The uracil moiety of the 5-substituted deoxyuridine compounds and of the 5-substituted β-D-arabinofuranosyluracil compounds may be converted to a cytosine moiety of the corresponding deoxycytidine and β-D-arabinofuranosylcytosine analogues, by conventional methods, the principles of which have been described for example by W. L. Sung (J. Chem. Soc. Chem. Commun. 1981, p. 1089 and J. Organic Chemistry 1982, volume 47, pages 3623-3628) and by P. Herdewijn et al. (J. Medicinal Chemistry 1985, volume 28, pages 550-555).

The 5-substituted 2'-deoxyuridine compounds may be prepared by condensation under anhydrous conditions from a bis-trimethylsilylated 5-substituted uracil compound with a suitably protected 2-deoxypentofuranosyl derivative, such as 2-deoxy-3, 5-di-O-p-toluoyl-D-erythropentofuranosyl chloride. This standard methodology has been used in various modifications. See for example, H. Verbruggen in Nucleoside analogues, Chemistry, Biology and Medical Applications, Plenum Press, N.Y. (1979), Eds. R. T. Walker, E. Declercq and F. Eckstein or A. J. Hubbard, A. S. Jones and R. T. Walker, Nucleic Acid Research, Volume 12, Number 17, pp. 6827–6837 (1984).

The 5-substituted 1-$\beta$-D-arabinofuranosyl compounds also may be prepared by condensation under anhydrous conditions of a bis-trimethylsilylated 5-substituted uracil compound with a suitably protected ribofuranosyl derivative such as 1-O-acetyl-2,3,5-tri-O-benzoyl-$\beta$-D-ribofuranose. After condensation the protecting groups are removed and a 2,2'-anhydrocompound is formed, which then is hydrolyzed to the desired 1-$\beta$-D-arabinofuranosyl uracil derivative. This too is a well known general procedure and it has been sued in the following examples detailing the synthesis of 1-$\beta$-D-arabinofuranosyl-5-isopropenyluracil, 1-$\beta$-D-arabinofuranosyl-5-ethyluracil and 1-$\beta$-D-arabinofuranosyl-5-hydroxymethyluracil.

Alternatively the 5-substituents may be introduced into unsubstituted 2'-deoxy-uracil or 1-$\beta$-D-arabinofuranosyl uracil by a metal catalyzed reaction, which has been used for preparation of a number of these derivatives and which has been described for example by Bergstrom. Another example of such a synthesis is described in the example below on the synthesis of 1-$\beta$-D-arabinofuranosyl-5-(1-propynyl)-uracil.

The uracil moiety of the 5-substituted 2'-deoxyuridine compounds and of the 5-substituted $\beta$-D-arabinofuranosyluracil compounds may be converted to a cytosine moiety of the corresponding 2'-deoxycytidine and $\beta$-D-arabinofuranosylcytosine analogues, by conventional methods, the principles of which have been described for example by W. L. Sung, J. Chem. Soc. Chem. Commun. (1981) p. 1089 and J. Organic Chemistry (1982) Vol. 47, pp. 3623–3628 and by P. Herdewijn et al., J. Med. Chemistry (1985) Vol. 28, pp. 550–555.

Alternatively, the 5-substituted 2'-deoxycytidine compounds and the 5-substituted 1-$\beta$-D-arabinofuranosyl cystosine compounds may be prepared by condensation of a 5-substituted cytosine derivative with a protected 2'-deoxyribopentofuranosyl derivative or a protected ribopentofuranosyl derivative in the same manner as was described above for the 5-substituted uracil derivatives.

The 5-substituted uracil compounds may be prepared by several methods, either by substitution into uracil or by synthesis and ring closure to the desired compound by the general Burckhalter method, an example of which is described by J. H. Burckhalter and H. L. Scarborough, J. Am. Pharm. Assoc, 1955, p. 545.

The following nucleoside compounds constitute part of the invention as prophylactic and therapeutic agents in control or treatment of retrovirus, especially HIV, or hepatitis B virus infections:

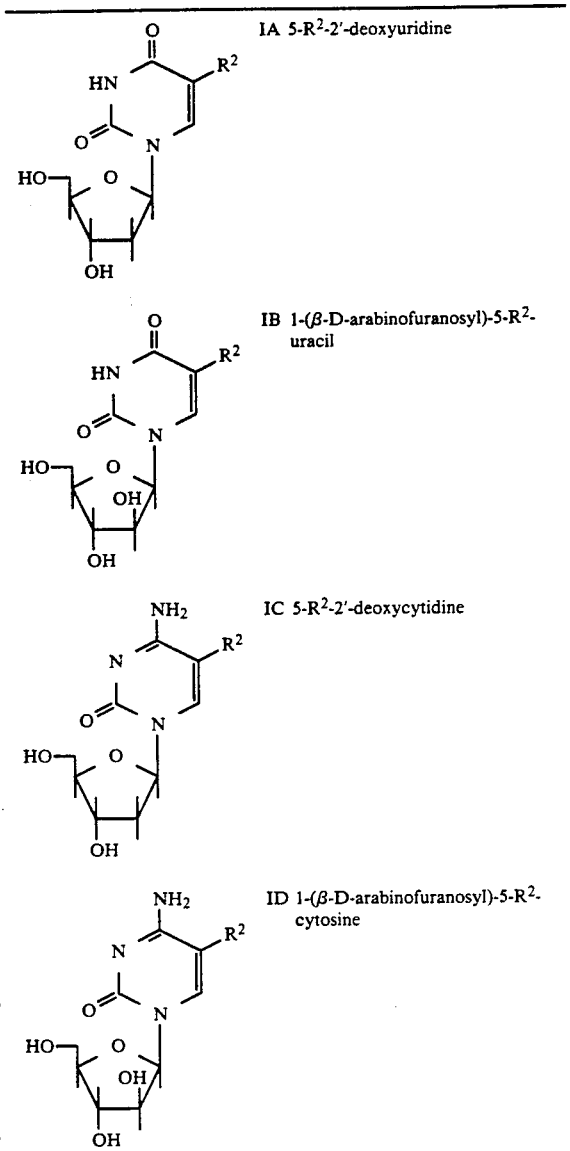

wherein $R^2$ may have the following meanings

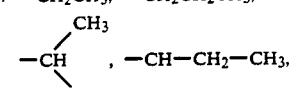

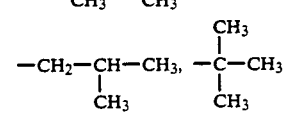

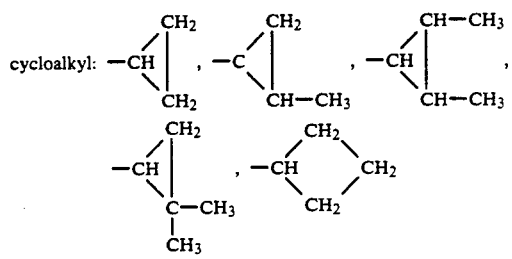

| phenyl, phenylalkyl: | 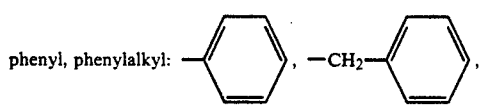 |

| R³ | R⁴ |
|---|---|
| H | OH |
| CH₃ | OH |
| CH₂CH₃ | OH |
| CH₂CH₂CH₃ | OH |
| H | CH₂OH |
| CH₃ | CH₂OH |
| CH₂CH₃ | CH₂OH |
| H | SH |
| CH₃ | SH |
| CH₂CH₃ | SH |
| CH₂CH₂CH₃ | SH |
| H | CH₂CH₂OH |
| CH₃ | CH₂CH₂OH |
| H | OCH₃ |
| CH₃ | OCH₃ |
| H | 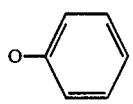 |
| CH₃ | 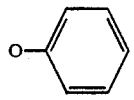 |
| H | CF₃ |
| CH₃ | CF₃ |
| CH₂CH₃ | CF₃ |
| H | CF₂CH₃ |
| CH₃ | CF₂CH₃ |
| H | F |
| H | Cl |
| H | Br |
| H | I |
| CH₃ | F |
| CH₃ | Cl |
| CH₃ | Br |
| CH₃ | I |
| CH₂CH₃ | F |
| CH₂CH₃ | Cl |
| CH₂CH₃ | Br |
| CH₂CH₃ | I |

| —CH=CH—R⁵ | R⁵ |
|---|---|
| | H |
| | CH₃ |
| | CH₂CH₃ |
| | CF₃ |
| | OCH₃ |
| | CH₂OH |
| | F |
| | Cl |

| —C=CH—R⁵<br>R⁵ | may be the same or different and chosen R⁵ among the following groups |
|---|---|
| | H |
| | CH₃ |
| | CH₂CH₃ |
| | CF₃ |
| | OCH₃ |
| | CH₂OH |
| | F |
| | Cl |

| —C≡C—R⁵ | R⁵ |
|---|---|
| | H |
| | CH₃ |
| | CH₂CH₃ |
| | CF₃ |
| | OCH₃ |
| | CH₂OH |
| | F |
| | Cl |

| —CH=C=CH₂ | |
| —CH—C=CH₂<br>\|<br>R⁵ | R⁵ |
|---|---|
| | H |
| | CH₃ |
| | CH₂CH₃ |
| | CF₃ |
| | OCH₃ |
| | CH₂OH |
| | F |
| | Cl |

Nucleosides containing uracil as base are preferred, as agents for use in control or treatment of retrovirus, especially HIV and hepatitis B virus infections in animal and man. The following nucleosides are the most preferred compounds: 5-cyclopropyl-2'-deoxyuridine, 5-ethyl-2'-deoxyuridine, 5-hydroxymethyl-2'-deoxyuridine, 5-(1-propenyl)-2'-deoxyuridine, 1-(β-D-arabinofuranosyl)-5-(1-propenyl)uracil, 5-isopropenyl-2'-deoxyuridine, or a physiologically acceptable salt thereof.

In clinical practice the nucleosides of the formula I will normally be administered orally, by injection or by infusion in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule. The compound may also be used without carrier material. As examples of pharmaceutical preparations may be mentioned tablets, dragees, capsules, granulates, suspensions, elixirs, syrups, solutions etc. Usually the active substance will comprise between 0.05 and 20% for preparations intended for injection and between 10 and 90% for preparations intended for oral administration.

In the treatment of patients suffering from retrovirus, especially HIV, or hepatitis B virus infections, it will be preferred to administer the compounds orally, parenterally or intravenously. The dosage at which the active ingredients are administered may vary within a wide range and will depend on various factors such as the severity of the infection, the age of patient etc., and may have to be individually adjusted. As a possible range for the amount of the compounds of the invention or a physiologically acceptable salt thereof to be administered per day may be mentioned from about 10 mg to about 10 000 mg, preferentially 100–500 mg for intravenous administration and preferentially 100–1000 mg for oral administration.

Salts

The physiologically acceptable salts are suitable acid addition salts, preferably derived from non-toxic acids. Such acid addition salts include, for example, those derived from hydrochloric acid, hydroiodic acid, sulphuric acid, p-toluenesulphonic acid, methane sulphonic acid, maleic acid, lactic acid, citric acid, tartaric acid, succinic acid, oxalic acid, p-chlorobenzenesulphonic acid, phosphoric acid, acetic acid, gluconic acid, pantothenic acid and lactobionic acid.

EXAMPLES

Example 1: Synthesis of 1-β-D-arabinofuranosyl-5-propynyluracil

A solution of Na (1.1 g) in CH$_3$OH (1000 ml) was added to a suspension of 5-propynyl-1-(2,3,5-tri-O-p-toluoyl-β-D-arabinofuranosyl) uracil (10.0 g) in CH$_3$OH (500 ml). The obtained solution was stirred at room temperature for a period of 4 h. The solution was then neutralized with Dowex 50 W×2 H+, filtered and evaporated. The solid residue was washed with Et$_2$O (100 ml) and hexane (400 ml) for 48 h. The obtained crystalline mass was filtered and dried to give 4.3 g of the title compound. M.p. 240°–245° C.

The compound 5-propynyl-1-(2,3,5-tri-O-p-toluoyl-β-D-arabinofuranosyl)uracil, used for synthesis of 1-β-D-arabinofuranosyl-5-propynyluracil, was prepared as follows:

1-(2,3,5-tri-O-p-toluoyl-β-D-arabinofuranosyl)uracil 30.0 g of p-toluoyl chloride was added to a solution of 1-β-D-arabinofuranosyluracil (14.8 g, from Sigma) in dry pyridine (300 ml), at 0° C. under nitrogen. The reaction mixture was allowed to reach room temperature and then heated at +50° C. for 2 h. CHCl$_3$ (450 ml) was then added and the CHCl$_3$ solution was washed with 1 M H$_2$SO$_4$ (2×400 ml) and H$_2$O (2×400 ml). The solution was dried (Na$_2$SO$_4$) and concentrated to a volume of about 150 ml. CH$_3$OH (700 ml) was added and chilling at −18° C. for 48 h afforded a crystalline mass which was filtered and dried to give 34.1 g of the title compound, m.p. 239°–242° C.

5-Iodo-1-(2,3,5-tri-O-toluoyl-(β-D-arabinofuranosyl)uracil

A solution of 1-(2,3,5-tri-O-p-toluoyl-β-D-arabinofuranosyl) uracil (23.9 g) and ICl (3.65 ml) in CH$_2$Cl$_2$ (350 ml) was refluxed for a period of 4 h. The solution was washed with a 2% NaHSO$_3$/H$_2$O solution (250 ml) and H$_2$O (3×400 ml). Drying (Na$_2$SO$_4$) and evaporation of the solvent gave a crude product which was recrystallized from CHCl$_3$ (50 ml) and CH$_3$OH (250 ml) to give 25.2 g of the title product. M.p. 215° C.

5-propynyl-1-(2,3,5-tri-O-p-toluoyl-(β-D-arabinofuranosyl)uracil

To a deoxygenated suspension of 5-iodo-1-(2,3,5-tri-p-toluoyl-β-D-arabinofuranosyl uracil (18.1 g), Cu(I)I (375 mg) and Pd(II)Cl$_2$(Ph$_3$P)$_2$ (375 mg) in Et$_3$N (1.15 l), at 25° C. and under N$_2$, was added about 5 mol of propyne generated from 2-dibromopropane (100 g) and KOH (90 g) in refluxing n-BuOH (300 ml) over a period of 2 h. The reaction mixture was then stirred at +40° C. for 24 h. The solvent was removed in vacuo and the residue was dissolved in CH$_2$Cl$_2$ (1.2 l). The solution was washed with 2% EDTA (2×500 ml), saturated NH$_2$Cl solution (4×400 ml) and water (4×400 ml). Drying (Na$_2$SO$_4$) and evaporation of the solvent gave a crude product which was purified on an alumina column using first CHCl$_3$ as the eluent flowed by CHCl$_3$/EtOH (9:1 v/v). The appropriate fractions were collected and evaporation of the solvent gave 10.0 g of the desired title compound. M.p. 219° C.

Example 2: Synthesis of 1-β-D-arabinofuranosyl-5-isopropenyluracil

A suspension of 15.2 g (0.10 mol) of 5-isopropenyl-pyrim-2,4-dione (according to Vidir Kristjansson, Organisk Kemi 1, University of Lund, Master of Science Thesis, Lund 1982), mixed with 100 ml of hexamethyldisilazane, 20 ml trimethylsilyl chloride, and 30 mg of ammonium sulphate, was refluxed for 15 hours (resulting in a homogeneous solution). The excess hexamethyldisilazane was removed under reduced pressure, 20 ml of toluene was added to the residue, and once again taken to dryness.

The product (2,4-bis-trimethylsilyloxy-5-isopropenylpyrimidine) was obtained quantitatively and was used immediately in the following reaction by dissolving it in 200 ml anhydrous acetonitrile together with 50.4 g (0.10 mol) of 1-O-acetyl-2,3,5-tri-O-benzoyl-β-D-ribofuranose (Sigma). A mixture of 26 g of stannic chloride in 100 ml of anhydrous acetonitrile was added dropwise to this cooled (icebath), stirred solution. After the addition, the cooling bath was removed and stirred overnight (14 hours). The reaction was quenched with 150 ml of water and the pH was adjusted to approximately 8 (bicarb). The layers were separated and the aqueous portion was extracted with chloroform (×3). The combined organic portions were combined, treated with brine and dried over MgSO$_4$. The solvent was removed under reduced pressure to give 61 g crude product. The crude product was separated on silica by means of flash chromatography using a gradient of chloroform with increasing amounts of ethyl acetate (starting with 0% and ending at 8%). This afforded 27.2 g of product (1-(2,3,5-tri-O-benzoyl-β-D-ribofuranosyl)-5-isopropenyluracil) in a 46% yield, NMR-200 MHz (CDCl3) PROTON: 6-H 9.46; =CH2 5.48/4.92; CH3 1.75; 1'-H 6.46 (J=6.1).

The protecting groups were removed by adding 27.2 g (45.6 mmol) of the above product to 400 ml sodium methoxide (freshly prepared) and overnight stirring at room temperature. To the reaction was added 100 ml of water and the pH was adjusted to just under 7 using DOWEX 50 (H+). The filtered and washed solution (80% aq. methanol) was taken to dryness under reduced pressure and 200 ml of water were added to the resiude. After neutralization (DOWEX 1/HCO$_3$), filtration, and washing with chloroform, the aqueous solution was once again evaporated under reduced pressure to give 9.7 g of desired (1-β-D-ribofuranosyl)-5-isopropenyluracil as a white solid (m.p. 212°–215° C.) in a 75% yield. NMR-200 MHz (D$_2$O CARBON-13; Cl' 91.8; C4' 86.3; C3' 76.1; C2' 71.5; C5' 62.6; C6 139.8; CH3 22.5/ PROTON: 6-H 8.11; —CH2 5.75/5.46; CH3 2.22; 1'-H 6.77 (J=2.9).

The 2,2'-anhydro compound was obtained by mixing 6.25 g (22.0 mmol) of the above product and 6.59 g (1.4 eq.) of diphenyl carbonate in 20 ml of anhydrous DMF and stirring at 140° in the presence of 0.3 g of sodium bicarbonate for 15 hours. The cooled reaction mixture was poured, with stirring, into 1.5 l of ether and the brown solid was filtered. The crude product was purified by flash chromatography on silica using 8% methanol in ethyl acetate to give 2.71 g of desired (2,2'-anhydro-2-hydroxy-1-β-D-arabinopentofuranosyl-5-isopropenyluracil) in a 46% yield. NMR-200 MHz (DMSO-d6) CARBON-13: Cl' 90.1; C4' 88.8; C3' 74.7; C2' 89.8; C5' 60.8; C5 123.9; C6 134.8; CH3 22.4/PROTON: 6-H 7.89; =CH2 5.71/5.25; CH3 2.12; 1'-H 6.50 (J=5.9).

The final compound was obtained by dissolving 800 mg (3.0 mmol) of the above product in 50 ml methanol and adding to it a solution of 17 ml of 1 N sodium hydroxide in 50 ml methanol. After 6 hours of stirring at room temperature, 25 ml of water were added and the solution was neutralized with DOWEX 50 (H+). After filtration and evaporation under reduced pressure, 610 mg of the title compound was obtained as a white solid (mp 204°-206° C.) in a 71% yield. NMR-200 MHz (CD3OD+DMSO-6) CARBON-13; Cl' 87.2; C4' 86.2; C3' 77.4; C2' 77.5; C5' 62.3; C5 114.7; C6 140.7; CH3 229/PROTON. 6-H 7.98; =CH2 5.88/5.20; CH3 210; 1'-H 6.30 (J=4.7).

Example 3: Synthesis of 1-β-D-arabinofuranosyl-5-isopropanoluracil

By acidic hydrolysis of 2,2-anhydro-2-hydroxy-1-β-D-arabinopentofuranosyl-5-isopropenyluracil, the hydrated compound, 1-β-D-arabinofuranosyl-5-isopropanoluracil, was obtained as follows:

The mixture of the 2,2'-anhydro compound (1.92 g, 7.2 mmol) and 150 ml of 1 M $H_2SO_4$ were refluxed for 2 hours. The solution was cooled to room temperature and neutralized with Dowex 1 (OH—) ion exchange resin. The solution was filtered and the resin was washed thoroughly with 80% aqueous methanol. The combined portions were evaporated to dryness to give 1.8 g of the desired compound as a semi-solid without any definite melting point in an 82.6% yield. NMR-200 MHz (CD3OD) CARBON-13; Cl' 87.5; C4' 86.3; C3' 77.8; C2' 77.4; C5' 62.8; C5 120.4; C6 139.4; C7 71.6/PROTON: 6-H 7.86; 2XCH3 1.46; 1'-H 6.14 (J=4.4).

Example 4; Effect of Compounds of the Formula I of HIV in H9 cells

Materials and Methods: HIV Infection of H9 Cells

H9 cells, $10^5$ cells per well on a 24 well plate, suspended in 2 ml RPMI-medium containing 10% fetal calf serum, 100 μg/ml penicillin, 10 μg/ml streptomycin sulfate and 2 μg/ml polybrene are exposed to HIV (HTLV-III$_B$) and different concentrations of the inhibiting compounds. The plates are incubated at 37° C. in 5% $CO_2$ for 6-7 days. The contents in each well is then homogenized with a pipette and transferred to a centrifuge tube. After centrifugation for 10 min at 1500 rpm the supernatent is removed and the cell pellet is analyzed by fixing in methanol on glass plates. Human HIV positive serum diluted 1:80 or 1:160 is added and incubated for 30 min at 37°. The plate is then washed with phosphate-buffered saline (PBS) containing $Ca^{2+}$ and $Mg^{2+}$. Sheep antihuman conjugate (FITC) is added and after a new incubation the plate is again washed with PBS. Contrast staining is done with Evans blue and after drying the frequency of HIV antigen containing cells is determined in a microscope. The test result is shown in Table 1.

TABLE 1

Concentration (μM) for 50% inhibition ($IC_{50}$) of human immunodeficiency virus multiplication in cell culture

| Compounds | $IC_{50}$ (μM) |
|---|---|
| 5-cyclopropyl-2'-deoxyuridine | <1 |
| 5-ethyl-2'-deoxyuridine | 1 |
| 5-hydroxymethyl-2'-deoxyuridine | <1 |
| 5-(1-propenyl)-2'-deoxyuridine | <1 |
| 1-(β-D-arabinofuranosyl)-5-(1-propenyl)-uracil | <1 |
| 5-(1-isopropenyl)-2'-deoxyuridine | 1-10 |
| 1-(β-D-arabinofuranosyl)-5-isopropenyluracil | 2 |
| 1-(β-D-arabinofuranosyl)-5-ethyluracil | 2 |

There is now data showing a correlation between inhibition of HIV transcriptase and HIV replication in cell cultures and the therapeutic effect in HIV infected patients. The compounds azidothymidine, dideoxycytidine and phosphonoformate are inhibitors of HIV reverse transcriptase (when the nucleoside analogues are in the form of triphosphates). They inhibit HIV replication in cell cultures and they have shown anti-HIV properties in patients. See Oberg, "Antiviral Therapy," AIDS Research. In press (1988). This is not surprising in view of the requirement of HIV reverse transcriptase for viral replication and the need for HIV multiplication for the development of the disease in infected persons.

Thus it seems likely that compounds which, analogous to azidothymidine, dideoxycytidine and phosphonoformate, inhibit HIV replication in cell cultures, also have a potential value for treatment of HIV infection in patients by way of inhibiting HIV replication. The compounds 5-(1-propenyl) 2'-deoxyuridine and 1-(β-D-arabinofuranosyl)-5-(1-propenyl) uracil are both moderately well absorbed in monkeys, oral bioavailability ranging from 30% to 60%. Elimination half-lives are 1.2-1.8 hours. Tao et al., J. Medical Virology 12, "Inhibition of Human Hepatitis B Virus DNA Polymerase and Duck Hepatitis B Virus DNA Polymerase by Triphosphates of Thymidine Analogs and Pharmacokinetic Properties of the Corresponding Nucleosides" (submitted for publication May 24, 1988). Thus the compounds have pharmacokinetic properties that are compatible with clinical treatment.

Example 5: Effect of Compounds of Formula I on Hepatitis B Virus in Animals Including Man.

There is no cell culture assay which can be used to determine the efficacy of compounds against hepatitis B virus. However, the hepatitis B virus encodes a reverse transcriptase, Summer and Mason, Cell 29 (1982) 403-415, obligatory for hepatitis b virus replication. This enzyme, which is also a consituent of the hepatitis B virus particles, can be used to evaluate the inhibitory activity against hepatitis B virus of nucleoside analogues provided that these compounds are used as their metabolic products, 5'-triphosphates. Table 2 shows the inhibitory effect of some nucleoside analog triphosphates on the activity of hepatitis B virus reverse transcriptase using a DNA template. The hepatitis B virus reverse transcriptase can, as all reverse transcriptases, use both RNA and DNA templates, and included in Table 2 is also the inhibition of duck hepatitis B virus polymerase using both DNA and RNA templates. The data show that the compounds are active inhibitors of hepatitis B virus polymerase, necessary for virus replication.

TABLE 2

Concentration (μM) for 50% inhibition (IC50) of hepatitis B virus reverse transcriptase using a DNA template and of duck hepatitis B virus reverse transcriptase using DNA and RNA templates.

| | IC50 (μM) | | |
|---|---|---|---|
| | Duck hepatitis virus polymerase | | Hepatitis B virus |
| Compound | DNA template | RNA template | polymerase DNA template |
| 5-Ethyl-2'-deoxythymidine | 0.9 | 0.74 | 0.25 |
| 5-Hydroxy-methyl-2'-deoxyuridine | 0.5 | 0.24 | 0.25 |
| 5-(1-propenyl)-2'-deoxyuridine | 0.11 | 0.15 | 0.1 |
| 1-(β-D-arabinofuranosyl)-5-(1-propenyl)uracil | 0.34 | 0.54 | 0.24 |

The assays were performed as described in Tao et al. Hepatitis B virus was for a long time considered to be a DNA virus with a viral DNA polymerase being part of the virus particles. However, it was discovered that the hepatitis B virus DNA polymerase activity was due to a reverse transcriptase and that this virus should be regarded as a retrovirus which, in contrast to other retroviruses, uses its DNA phase as genetic material in the virus particles. Summers and Mason. Hepatitis B viruses are therefore not related to DNA viruses such as herpes-viruses or adeno-virus, but rather are related to retroviruses such as HIV.

Recent investigations have also shown a great similarity in the pattern of inhibition of HIV reverse transcriptase and hepatitis B virus transcriptase when comparing the effect of different inhibitors. Nordenfelt et al., J. Med. Virol. 22 (1987) 231–236; Vrang et al., Antimicro. Agent Chemother. 29 (1986) 867–872.

We claim:

1. A compound having the formula

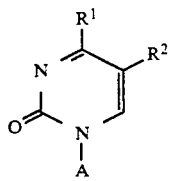

wherein
R¹ is OH
R² is cyclopropyl; and
A is β-D-arabinofuranosyl; or a physiologically acceptable salt thereof.

2. A pharmaceutical composition which comprises an effective antiviral amount of a compound according to claim 1, and a physiologically acceptable carrier.

3. A compound having the formula

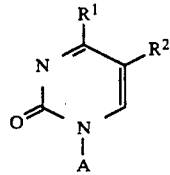

wherein
R¹ is NH₂;
R² is cyclopropyl; and
A is β-2'-deoxy-D-ribofuranosyl; or a physiologically acceptable salt thereof.

4. A pharmaceutical composition which comprises an effective antiviral amount of a compound according to claim 3, and a physiologically acceptable carrier.

5. A method for the treatment of hepatitis B virus infections, which comprises administering to a patient in need of such treatment, an effective anti-hepatitis B amount of a compound having the formula

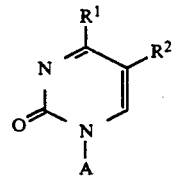

wherein
A is selected from the group consisting of β-2'-deoxy-D-ribofuranosyl and β-D-arabinofuranosyl;
R¹ is selected from the group consisting of hydroxy and amino; and
R² is selected from the group consisting of cycloalkyl, $C_1$–$C_5$ alkyl-substituted cycloalkyl, a saturated or unsaturated, straight or branched alkyl containing 1–5 carbon atoms unsubstituted or substituted with halogen, hydroxy, mercapto, trifluoroalkyl or difluoroalkyl containing 1–3 carbon atoms, phenoxy or alkoxy containing 1–3 carbon atoms, phenyl and phenylalkyl containing 1–3 carbon atoms in the alkyl substituent; or a physiologically acceptable salt thereof.

6. The method according to claim 5 comprising administration of the compound wherein R¹ is hydroxy; or a physiologically acceptable salt thereof.

7. The method according to claim 5 comprising administration of the compound wherein R² is selected from the group consisting of cycloalkyl, hydroxyalkyl, a saturated alkyl containing 1–3 carbon atoms, and an unsaturated alkyl containing 2–3 carbon atoms; or a physiologically acceptable salt thereof.

8. The method according to claim 5 comprising administration of a compound selected from the group consisting of 5-cyclopropyl-2'-deoxyuridine, 5-ethyl-2'-deoxyuridine, 5-hydroxymethyl-2'-deoxyuridine, 5-(1-propenyl)-2'-deoxyuridine, 1-(β-D-arabinofuranosyl)-5-(1-propenyl)-uracil, and 5-isopropenyl-2'-deoxyuridine.

9. The method according to claim 5 comprising oral administration.

10. The method according to claim 5 comprising intravenous administration.

11. The method according to claim 5 comprising parenteral administration.

12. The method according to claim 5, wherein said compound is 1-(β-D-arabinofuranosyl)-5-(1-propynyl)-uracil, or a physiologically acceptable salt thereof.

13. The method according to claim 5, wherein said compound is 5-cyclopropyl-2'-deoxuridine, or a physiologically acceptable salt thereof.

14. The method according to claim 5, wherein said compound has the formula

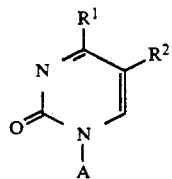
wherein
R¹ is OH;
R² is cyclopropyl; and
A is β-D-arabinofuranosyl; or a physiologically acceptable salt thereof.
15. The method according to claim 5, wherein said compound has the formula
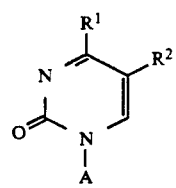
wherein
R¹ is NH₂;
R² is cyclopropyl; and
A is β-2'-deoxy-D-ribofuranosyl; or a physiologically acceptable salt thereof.
* * * * *